US00PP28343P3

(12) United States Plant Patent
Barbour

(10) Patent No.: US PP28,343 P3
(45) Date of Patent: Aug. 29, 2017

(54) OAK TREE NAMED 'DAHLONEGA'

(50) Latin Name: *Quercus lyrata*
Varietal Denomination: Dahlonega

(71) Applicant: John Barbour, Hawkinsville, GA (US)

(72) Inventor: John Barbour, Hawkinsville, GA (US)

(73) Assignee: Athena Trees, Inc., Hawkinsville, GA (US)

( * ) Notice: Subject to any disclaimer, the term of this patent is extended or adjusted under 35 U.S.C. 154(b) by 107 days.

(21) Appl. No.: 14/545,866

(22) Filed: Jun. 30, 2015

(65) Prior Publication Data

US 2017/0006750 P1 Jan. 5, 2017

(51) Int. Cl.
*A01H 5/00* (2006.01)

(52) U.S. Cl.
USPC ..... Plt./225

(58) Field of Classification Search
USPC ..... Plt./225
See application file for complete search history.

*Primary Examiner* — June Hwu
(74) *Attorney, Agent, or Firm* — C. A. Whealy

(57) ABSTRACT

A new and distinct cultivar of Oak tree named 'Dahlonega', characterized by its upright branching habit and pyramidal tree form; freely branching habit with numerous secondary branches providing a full and densely foliated appearance; early leaf-out in the spring, typically about two to three weeks earlier than other selections of *Quercus lyrata*; and numerous glossy dark green-colored leaves that become dark orange and red in color during the autumn.

5 Drawing Sheets

Botanical designation: *Quercus lyrata.*
Cultivar denomination: 'DAHLONEGA'.

BACKGROUND OF THE INVENTION

The present invention relates to anew and distinct cultivar of Oak tree, botanically known as *Quercus lyrata*, commercially referred to as Swamp Post Oak or Overcup Oak and hereinafter referred to by the name 'Dahlonega'.

The new Oak tree is a product of a planned breeding program conducted by the Inventor in Pulaski and Oconee Counties, Ga. The objective of the breeding program is to create new Oak trees appropriate for urban landscapes that leaf-out early in the spring and have attractive autumn leaf color.

The new Oak tree originated from an open-pollination of an unnamed selection of *Quercus lyrata*, not patented, as the female, or seed, parent with an unknown selection of *Quercus lyrata* as the male, or pollen, parent. The new Oak tree was discovered and selected by the Inventor as a single plant from within the progeny of the stated open-pollination in a controlled environment in Pulaski County, Ga. in November, 2006.

Asexual reproduction of the new Oak tree by grafting in a controlled environment in Oconee County, Ga. since has shown that the unique features of this new Oak tree are stable and reproduced true to type in successive generations.

SUMMARY OF THE INVENTION

Trees of the new Oak have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'Dahlonega'. These characteristics in combination distinguish 'Dahlonega' as a new and distinct Oak tree:

1. Upright branching habit and pyramidal tree form.
2. Freely branching habit with numerous secondary branches providing a full and densely foliated appearance.
3. Early leaf-out in the spring, typically about two to three weeks earlier than other selections of *Quercus lyrata.*
4. Numerous glossy dark green-colored leaves that become dark orange and red in color during the autumn.

Trees of the new Oak can be compared to trees of the female parent selection. Trees of the new Oak differ primarily from trees of the female parent selection in the following characteristics:

1. Trees of the new Oak are upright pyramidal in shape with narrow branch angles whereas trees of the female parent selection are broadly rounded in shape with much wider branch angles.
2. Trees of the new Oak leaf-out in the spring two to three weeks earlier than trees of the female parent selection.
3. Leaves of trees of the new Oak become dark orange and red in color during the autumn whereas leaves of trees of the female parent selection do not change color in the autumn.

Trees of the new Oak can also be compared to trees of *Quercus lyrata* 'Red Baron', not patented. Trees of the new Oak and 'Red Baron' differ primarily in the following characteristics:

1. Trees of the new Oak are upright pyramidal in shape with narrow branch angles whereas trees of 'Red Baron' are oval in shape with much wider branch angles.
2. Trees of the new Oak leaf-out in the spring one to two weeks earlier than trees of 'Red Baron'.
3. Leaves of trees of the new Oak are smaller than leaves of trees of 'Red Baron'.

4. Leaves of trees of the new Oak and 'Red Baron' differ in autumn leaf color as shown in the following photographs.

BRIEF DESCRIPTION OF THE PHOTOGRAPHS

The accompanying colored photographs illustrate the overall appearance of the new Oak tree showing the colors as true as it is reasonably possible to obtain in colored reproductions of this type. Colors in the photographs may differ slightly from the color values cited in the detailed botanical description which accurately describe the colors of the new Oak tree.

The photograph on the first sheet is a side perspective view of a typical mature tree of 'Dahlonega' grown during the summer in an outdoor nursery.

The photographs on the second sheet are side perspective views of typical mature trees of 'Dahlonega' (left) and 'Red Baron' (right) grown during the winter in an outdoor nursery showing the differences in branch angle orientation and overall tree form.

The photographs on the third sheet are close-up views of the upper surfaces of typical leaves of 'Dahlonega' (left) and 'Red Baron' (right) grown during the summer in an outdoor nursery showing the differences in leaf size.

The photographs on the fourth sheet are close-up views of the upper surfaces of typical leaves of 'Dahlonega' (left) and 'Red Baron' (right) grown during the autumn in an outdoor nursery showing the differences in autumn leaf color.

The photographs on the fifth sheet are side perspective views of typical mature trees of 'Dahlonega' (top) and 'Red Baron' (bottom) on Apr. 14, 2015 in an outdoor nursery showing the differences in spring leaf development.

DETAILED BOTANICAL DESCRIPTION

The aforementioned photographs and following observations, measurements and values describe trees grown in an outdoor nursery in Pulaski County, Ga. and under cultural practices typical of commercial Oak tree production. Trees used in the photographs and description were eight years old. During the production of the trees, average day temperature was 24.5° C. and average night temperature was 11.1° C. In the following description, color references are made to The Royal Horticultural Society Colour Chart, 2007 Edition, except where general terms of ordinary dictionary significance are used.

Botanical classification: *Quercus lyrata* 'Dahlonega'.

Parentage:

*Female, or seed, parent*.—Unnamed selection of *Quercus lyrata*, not patented.

*Male, or pollen, parent*.—Unknown selection of *Quercus lyrata*, not patented.

Propagation:

*Type*.—By grafting scions of the new Oak tree onto an unnamed selection of *Quercus lyrata* rootstock.

Tree description:

*Tree form and growth habit*.—Deciduous tree with upright branching habit and pyramidal tree form; freely branching habit with about 68 lateral branches developing per tree; full and densely-foliated appearance; vigorous growth habit; early leaf-out in the spring; to date, flower initiation and development have not been observed on trees of the new Oak.

*Tree height*.—About 9.75 meters.

*Tree width* (*spread*).—About 5.97 meters.

*Trunk caliper*.—About 27.9 cm.

*Growth rate, height*.—About 1.22 meters per year.

*Growth rate, caliper*.—About 3.49 cm per year.

*Branch angle orientation*.—Lower canopy branches, about 23° from vertical; upper canopy branches, about 18° from vertical.

*Internode length*.—About 2.5 cm on one-year old wood.

*Lateral branch color*.—Immature bark: Close to between 172B and 176 and between 177A and 164A. Mature bark: Close to 198B; underneath, close to between 198A and 195A.

*Immature bark texture*.—Smooth, glabrous.

*Mature bark texture*.—Rough, woody, flaky.

*Branch lenticels*.—Size: On one-year growth, about 0.5 mm by 0.5 mm; on three to four-year old growth, about 1.5 mm to 2 mm by 0.75 mm. Shape: On one-year growth, circular; on three to four-year old growth, oblong. Color: On one-year growth, close to NN155B; on three to four-year old growth, close to 192D.

*Dormant leaf buds*.—Length: About 2 mm. Diameter: About 2.2 mm. Shape: Broadly ovate with rounded apex. Texture: Smooth. Color: Close to N200C; edges, close to between 183C and 200D.

*Leaf arrangement*.—Alternate, simple.

*Leaf length*.—About 13.86 cm.

*Leaf width*.—About 9.05 cm.

*Leaf shape*.—Obovate.

*Leaf apex*.—Obtuse.

*Leaf base*.—Cuneate.

*Leaf margins*.—Entire; deeply three to five-lobed with wide rounded sinuses.

*Leaf venation*.—Pinnate.

*Leaf texture, upper surface*.—Smooth, glabrous.

*Leaf texture, lower surface*.—Puberulent.

*Leaf luster, upper surface*.—Glossy.

*Leaf luster, lower surface*.—Slightly glossy.

*Leaf color*.—When developing, upper surface: Close to between 138A and 137A. When developing, lower surface: Close to 138A. Fully developed, upper surface: Close to 137A; in the autumn, close to 173A to 173B and 179A; venation, close to 162B. Fully developed, lower surface: Close to 137C; venation, close to 164C.

*Leaf petioles*.—Length: About 8.47 cm. Diameter: About 1.59 mm. Texture, upper and lower surfaces: Smooth, glabrous. Color, upper surface: Close to 59A and 145C. Color, lower surface: Close to 145C.

Temperature tolerance: Trees of the new Oak have been observed to tolerate high temperatures about 40.5° C. and low temperatures about −11.7° C. when grown in USDA Hardiness Zone 8.

Pathogen & pest resistance: To date, trees of the new Oak have been not observed to be resistant to pathogens and pests common to Oak trees.

It is claimed:

1. A new and distinct Oak tree named 'Dahlonega' as illustrated and described.

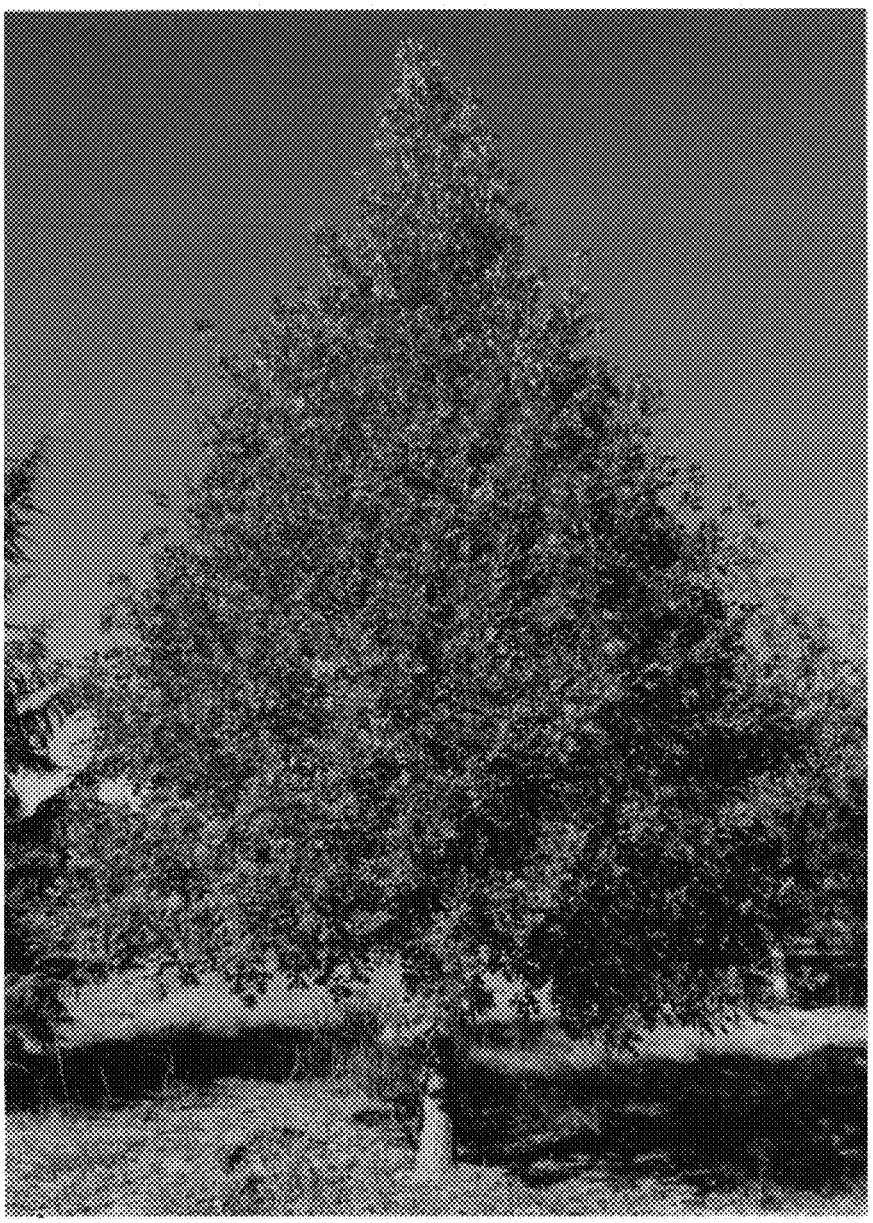

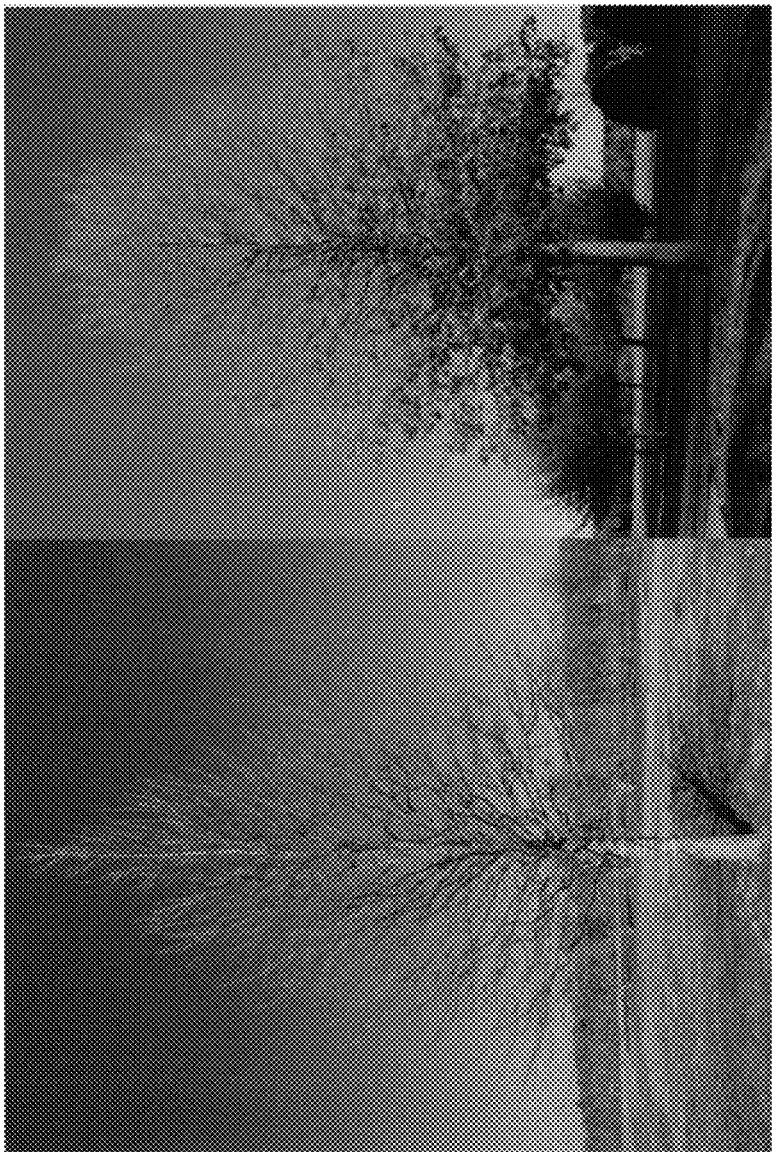

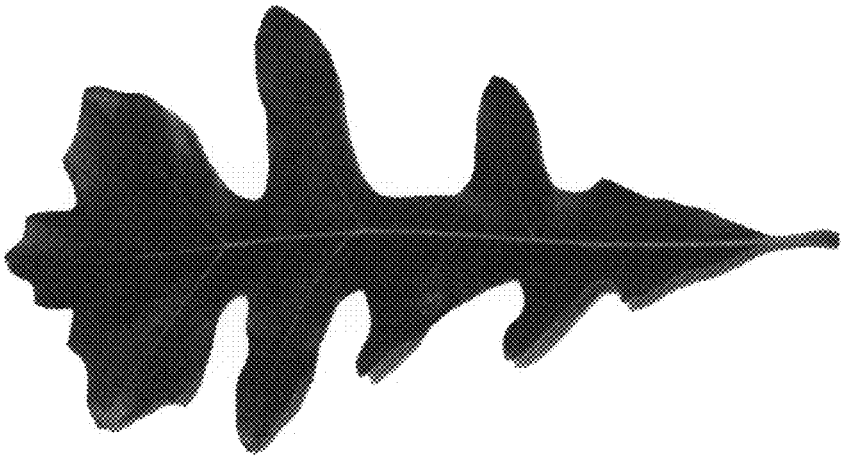
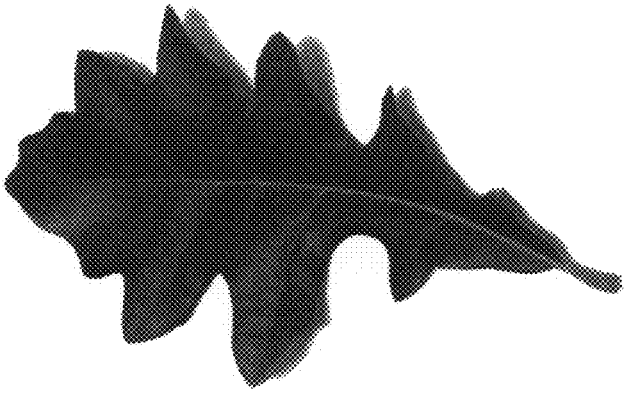

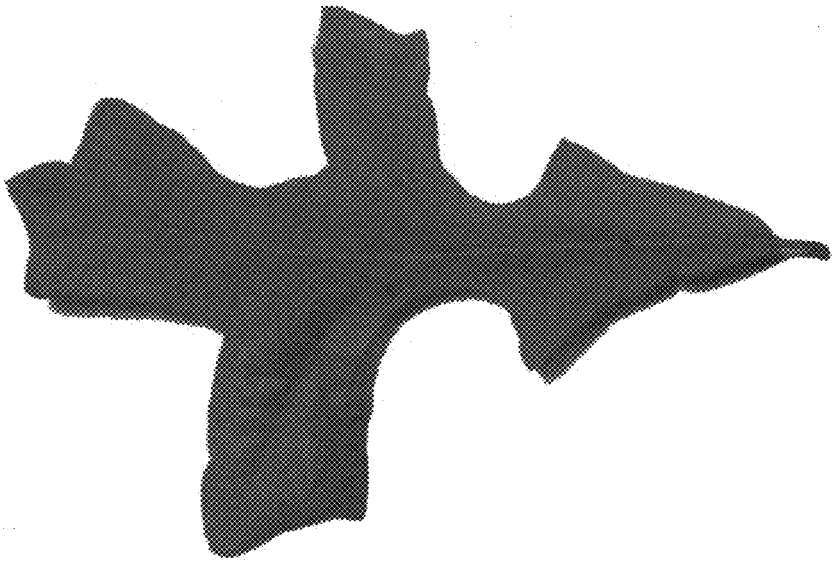
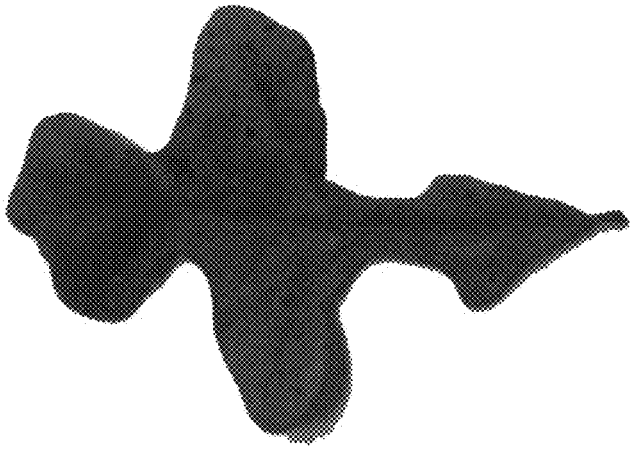

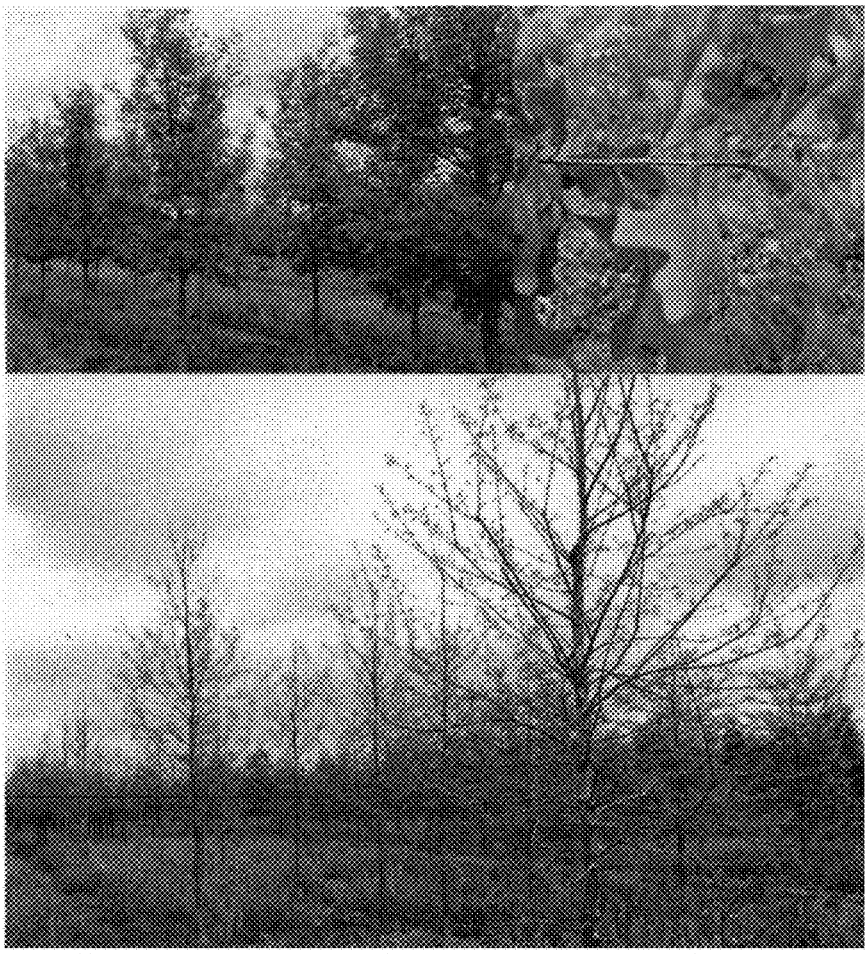

* * * * *